(12) United States Patent
Sathaye et al.

(10) Patent No.: US 7,941,219 B2
(45) Date of Patent: May 10, 2011

(54) CAPTURE DETECTION BASED ON PROPAGATED DEPOLARIZATION FROM A REMOTE PACING SITE

(75) Inventors: Alok S. Sathaye, Minneapolis, MN (US); M. Jason Brooke, Minneapolis, MN (US); Scott A. Meyer, Lakeville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1201 days.

(21) Appl. No.: 11/517,699

(22) Filed: Sep. 8, 2006

(65) Prior Publication Data

US 2008/0065166 A1 Mar. 13, 2008

(51) Int. Cl.
*A61N 1/00* (2006.01)
(52) U.S. Cl. .......................................... 607/28
(58) Field of Classification Search .................... 607/28, 607/5, 29
See application file for complete search history.

(56) References Cited

U.S. PATENT DOCUMENTS

| | | | |
|---|---|---|---|
| 6,091,990 A | 7/2000 | Hsu et al. | |
| 6,148,234 A * | 11/2000 | Struble | 607/28 |
| 6,768,924 B2 | 7/2004 | Ding et al. | |
| 6,885,893 B1 * | 4/2005 | Lu | 607/28 |
| 6,915,164 B2 * | 7/2005 | Bradley et al. | 607/29 |
| 2001/0049543 A1 * | 12/2001 | Kroll | 607/28 |

* cited by examiner

*Primary Examiner* — Mark W Bockelman
*Assistant Examiner* — Roland Dinga
(74) *Attorney, Agent, or Firm* — Hollingsworth & Funk, LLC

(57) ABSTRACT

A methods and devices for capture detection are based on sensing a propagated depolarization from a contralateral cardiac chamber. An intersite sensing interval is determined based on an intersite pacing delay and an intersite conduction delay associated with first and second pacing sites. Pacing pulses are delivered to the first pacing site and the second pacing site, the pacing pulses separated in time by the intersite pacing delay. An intersite sensing interval is timed. The process includes sensing, during the intersite sensing interval, at the first pacing site for a depolarization propagated to the first pacing site from the second pacing site. It a depolarization propagated from the second pacing site is not sensed, then capture of the first and second pacing sites is detected.

22 Claims, 12 Drawing Sheets

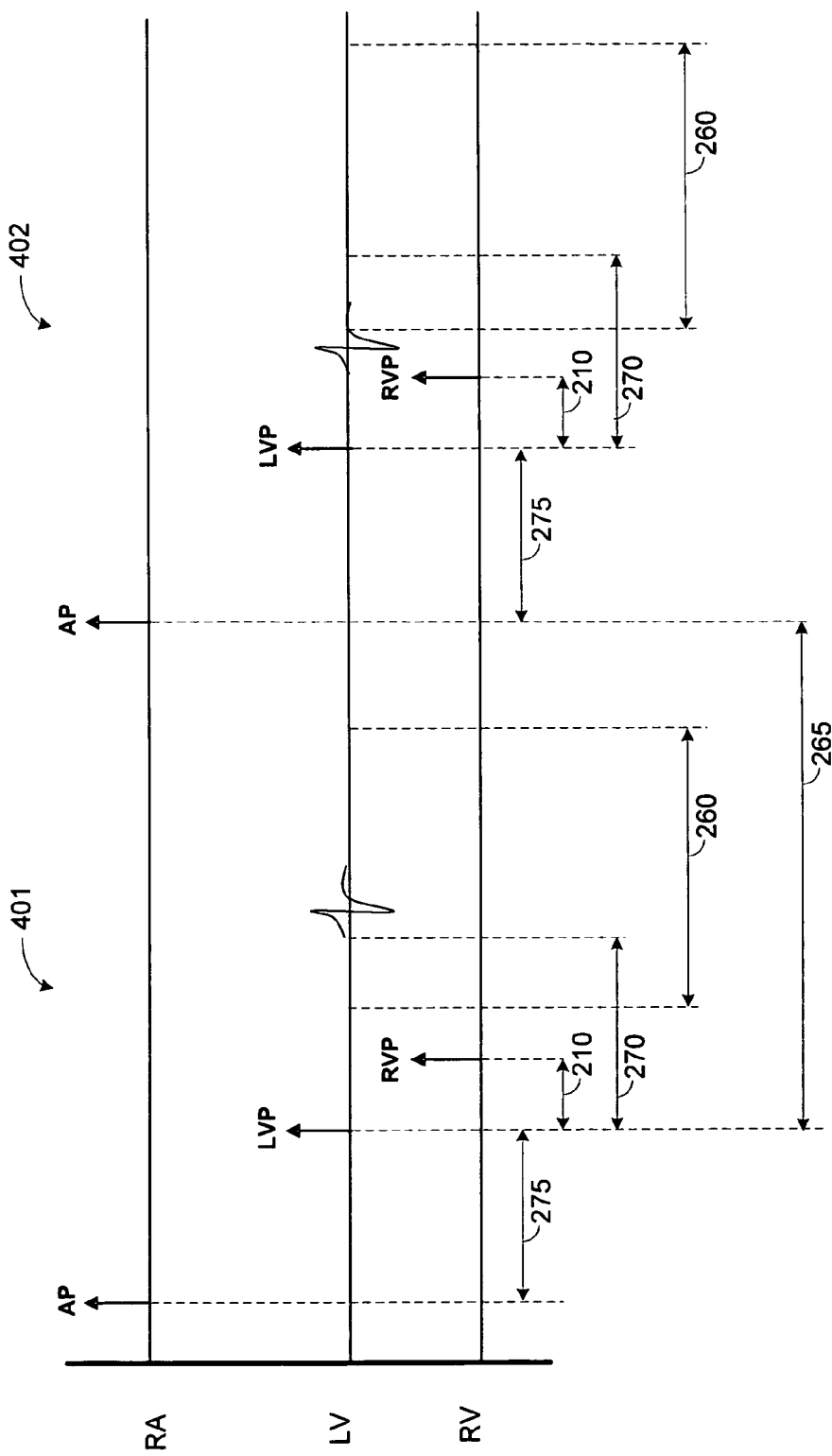

CAPTURE DETECTION BASED ON PROPAGATED DEPOLARIZATION FROM A REMOTE PACING SITE

FIELD OF THE INVENTION

The present invention relates generally to implantable medical devices and, more particularly, to capture threshold tests for determining capture of one or more heart chambers.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. A pacing pulse that causes a sufficient depolarization of the myocardium, producing a propagating wave of excitation produces a contraction. A pacing pulse that does not produce capture wastes energy from the limited energy resources (battery) of a pacemaker, and can have deleterious physiological effects as well. A pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration or width. Programmable pacemakers enable the amplitude and pulse width of pacing pulses to be adjusted, along with other parameters. It is therefore desirable to perform a capture verification test at selected times in order to ascertain whether capture is being achieved by a pacemaker so that such parameters can be adjusted if needed.

It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

SUMMARY OF THE INVENTION

The present invention involves various methods and devices for detecting capture of one or more heart chambers. One embodiment of the invention is directed to a method, implementable in a pacemaker, for detecting capture. An intersite sensing interval is determined based on an intersite pacing delay and an intersite conduction delay associated with first and second pacing sites. Pacing pulses are delivered to the first pacing site and the second pacing site, the pacing pulses separated in time by the intersite pacing delay. An intersite sensing interval is timed. The process includes sensing, during the intersite sensing interval, at the first pacing site for a depolarization propagated to the first pacing site from the second pacing site. It a depolarization propagated from the second pacing site is not sensed, capture of the first and second pacing sites is detected. The intersite pacing delay may be selected to shift the interaction point of the depolarization propagated from the second pacing site and a depolarization propagated from the first pacing site.

Non-capture of the first pacing site may be detected if the depolarization propagated from the second pacing site is sensed within the intersite sensing interval. Fusion may be detected if the depolarization propagated from the second pacing site is sensed outside the intersite sensing interval.

The capture detection method may be used in conjunction with a capture threshold test wherein the amplitude of the pacing pulses delivered to the first pacing site are modified during successive cardiac cycles until loss of capture of the first pacing site is detected. The capture threshold of the first pacing site may be determined after loss of capture at the first pacing site is detected.

According to one aspect of the invention, the conduction delay may be measured. For example, the conduction delay may be measured during an initialization process of a capture threshold test.

Another embodiment of the invention involves a pacemaker that detects capture. The pacemaker includes electrodes electrically coupled to a heart at a first pacing site and a second pacing site. Pacing circuitry is configured to deliver pacing pulses to the first pacing site and the second pacing site during a cardiac cycle via the electrodes. The pacing pulses to the first and second sites are separated in time by an intersite pacing delay. Timer circuitry times an intersite sensing interval which is determined based on the intersite pacing delay and a conduction delay associated with the first and second pacing sites. Sense circuitry is used to sense at the first pacing site during the intersite sensing interval for a depolarization propagated from the second pacing site responsive to the pacing pulse delivered to the second pacing site. Capture detection circuitry detects capture of the first and second pacing sites if the depolarization propagated from the second pacing site is not sensed.

The pacemaker may also include measurement circuitry configured to measure the conduction delay associated with the first and second pacing sites;

The first pacing site and second pacing sites may be in contralateral heart chambers. For example, the first pacing site may be in a ventricle with the second site in a contralateral ventricle. In another example, the first pacing site may be in an atrium with the second pacing site in a contralateral atrium. In yet another example, both pacing sites may be in the same cardiac chamber.

According to one aspect of the invention, the capture detection circuitry is configured to detect non-capture of the first pacing site if the depolarization propagated from the second pacing site is detected during the intersite sensing interval. According to another aspect of the invention, the capture detection circuitry is configured to detect fusion if a depolarization signal is detected outside the intersite sensing interval.

The pacemaker may also include circuitry configured to control a capture threshold test. The control circuitry configured to modify an energy of the pacing pulse delivered to the first pacing site until loss of capture is detected.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 4B is a timing diagram illustrating, for two cardiac cycles the use of an intersite sensing interval for capture and/or fusion detection in accordance with some embodiments;

Figure 1:
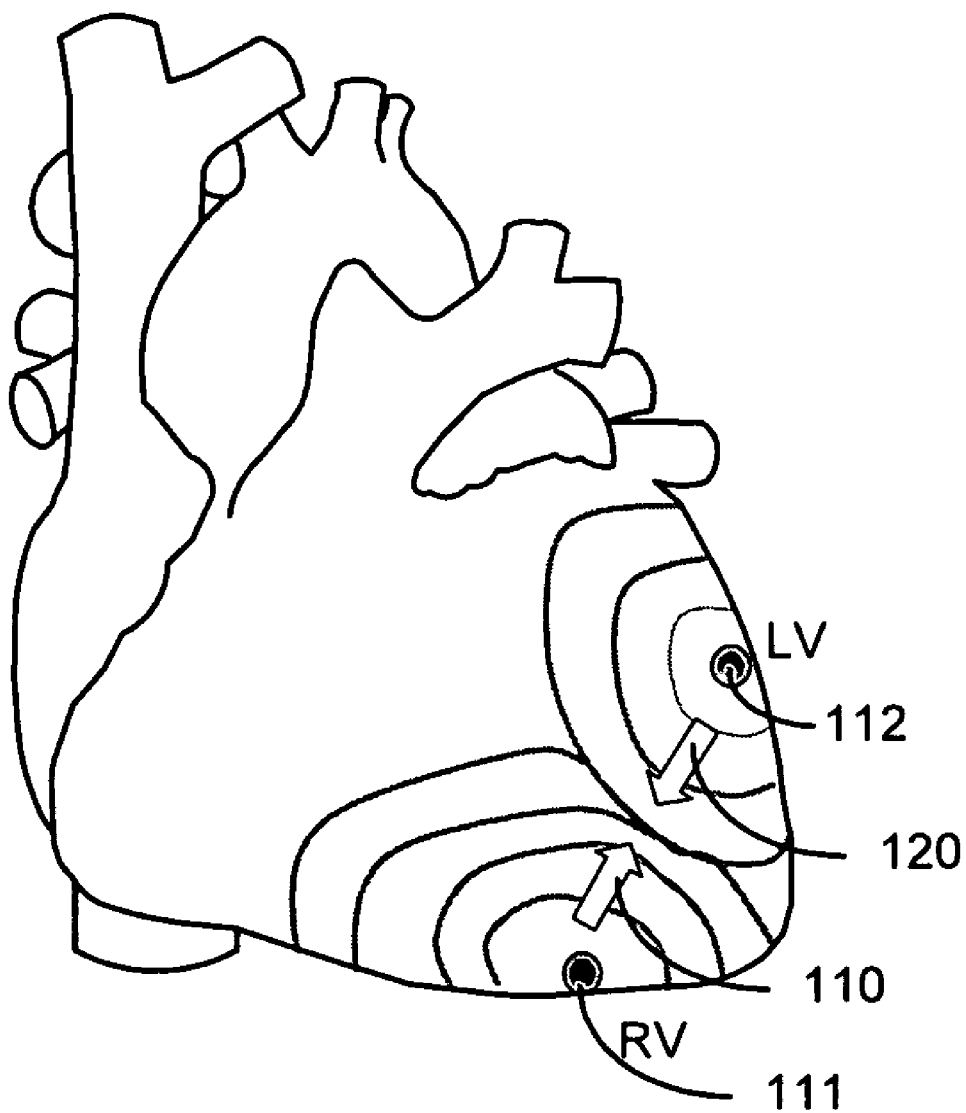
FIG. 1 is a diagram illustrating a propagating wavefront of electrical activation produced by capture of the right ventricle moving toward the left ventricle.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Capture detection methodologies in accordance with embodiments of the invention are based on cancellation of depolarization wavefronts caused by pacing pulses delivered to two or more pacing sites. In some implementations, the pacing sites may involve sites within a single cardiac chamber. In some implementations, the pacing sites may be located in contralateral cardiac chambers, e.g., right and left ventricles or right and left atria. In one embodiment, after delivering pacing pulses separated by an interventricular delay to right and left ventricles, the system senses for cardiac activity in the first-paced ventricle during an intersite sensing interval which may be timed relative to the pacing pulse delivered to the first-paced ventricle.

If both pacing pulses captured their respective chambers, the depolarization wavefront propagating from second-paced ventricle collides with refractory tissue caused by the depolarization wavefront propagating from the first-paced ventricle. When this occurs, the depolarization propagated from the second-paced ventricle is not sensed during the intersite sensing interval. If the first-paced ventricle was not captured, then the depolarization propagated from the second-paced ventricle is not canceled by the refractory tissue, and cardiac activity responsive to the activation of the second-paced ventricle is evident in the intersite sensing interval. Although the above example was explained in terms of pacing sites in the ventricles, the approach is also applicable to pacing sites in opposite atria and/or multiple intrachamber pacing sites within one heart chamber. The approaches described herein are useful for capture detection in patients that have or do not have disrupted conduction between the pacing sites, e.g., intra-atrial block, right bundle branch block, left bundle branch block between bilateral chambers.

The processes involved in capture detection approaches of the present invention are illustrated in the diagrams of FIGS. 1-4. FIGS. 1-4 pertain to biventricular pacing, however, the concepts are similarly applicable to biatrial pacing or pacing multiple sites within a cardiac chamber. As illustrated in FIG. 1, following biventricular pacing, capture of the right ventricle produces a propagating wavefront of depolarization 110 moving toward the left ventricle. Capture of the left ventricle produces a propagating wavefront of depolarization 120 moving toward the right ventricle. The depolarization wavefronts 110, 120 from the right and left ventricles collide and interact at a point between the pacing electrodes 111, 112. At the point of interaction, each wavefront 110, 120 meets refractory tissue and the wavefronts 110, 120 annihilate one another.

Figure 2:
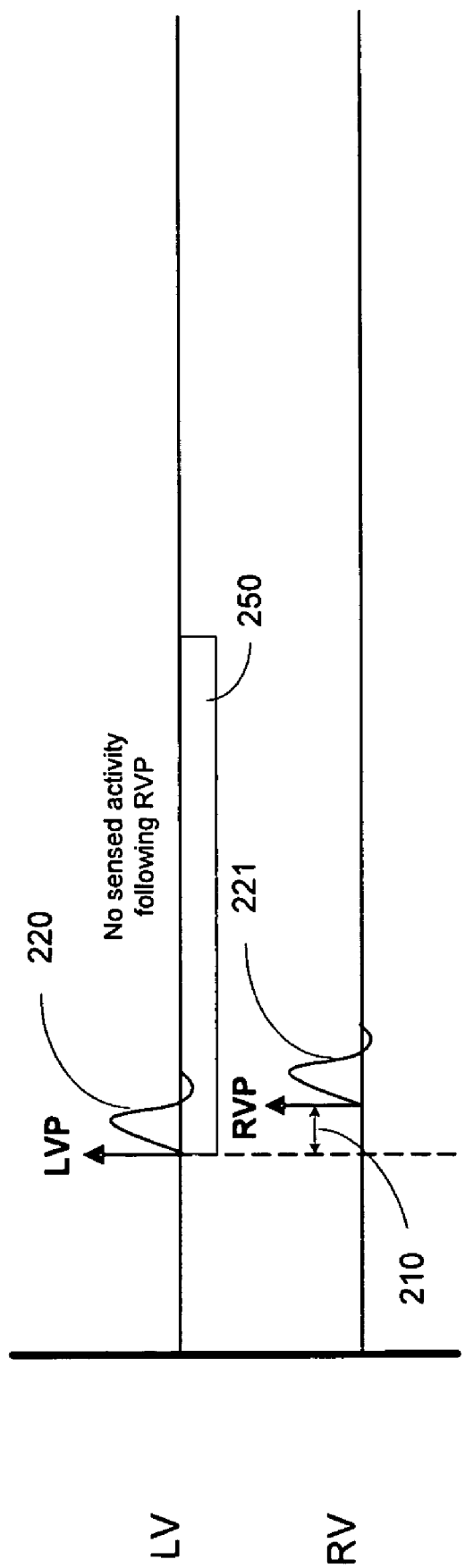
FIG. 2 illustrates a timing diagram of paced events and sensed signals in the right and left ventricles illustrating capture of both ventricles.

FIG. 2 illustrates a timing diagram for pacing and/or sensing in the right and left ventricles illustrating capture of both ventricles. In this scenario, a left ventricular pacing pulse (LVP) is delivered to the left ventricle. A right ventricular pacing pulse (RVP) is delivered to the right ventricle delayed from the time of delivery of the LVP. For example, in one implementation, the interventricular pacing delay 210 between the LVP and the RVP may be greater than about 40 ms. In other implementations, delivery of the LVP and RVP may be separated in time by an interventricular delay 210 of up to about 500 ms. The interventricular delay 210 tends to exaggerate the conduction delay between ventricles. Appropriate selection of the interventricular delay 210 enhances the capture detection processes of the present invention in patients who do not experience excessively delayed conduction between the ventricles, e.g., patients who do not have LBBB or RBBB.

If the LVP captures the left ventricle, a depolarization wavefront 220 is initiated at the left ventricular pacing site and propagates toward the right ventricle. If the left ventricle is captured by the LVP, the cardiac tissue near the left ventricular electrode becomes refractory for a period of time 250 following capture of the left ventricle.

If the RVP captures the right ventricle, a depolarization wavefront 221 is initiated at the right ventricular pacing site and travels toward the left ventricular site. The refractoriness of the left ventricular tissue after capture of the left ventricle prevents the depolarization wavefront 221 initiated by the RVP from activating the refractory left ventricular tissue. In FIG. 2, no depolarization is sensed in the left ventricle following the RVP. If the depolarization of the right ventricle does not propagate to the left ventricle, then capture of both ventricles has occurred. In various embodiments, either the left ventricle or the right ventricle may be paced first.

Figure 3:
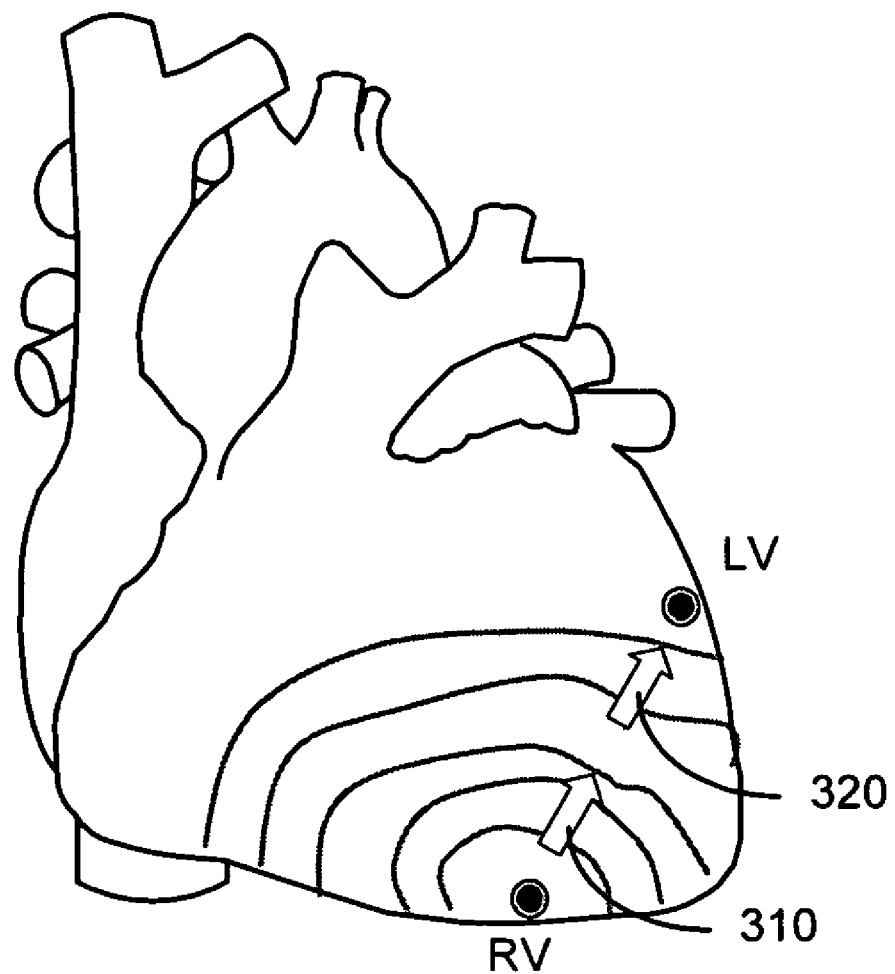
FIG. 3 is a diagram illustrating capture of the right ventricle with non-capture of the left ventricle during a cardiac cycle.

FIG. 3 illustrates capture of the right ventricle with non-capture of the left ventricle during a cardiac cycle. Capture of the right ventricle initiates a propagating wavefront of depolarization that starts 310 in the right ventricle and travels toward the left ventricle. If the left ventricle is not captured by a pacing pulse delivered to the left ventricle, there is no opposing depolarization wavefront traveling from the left ventricle to the right ventricle. The left ventricular tissue does not become refractory and the depolarization wavefront initiated by right ventricular capture continues 320 to the left ventricle.

Figure 4A:
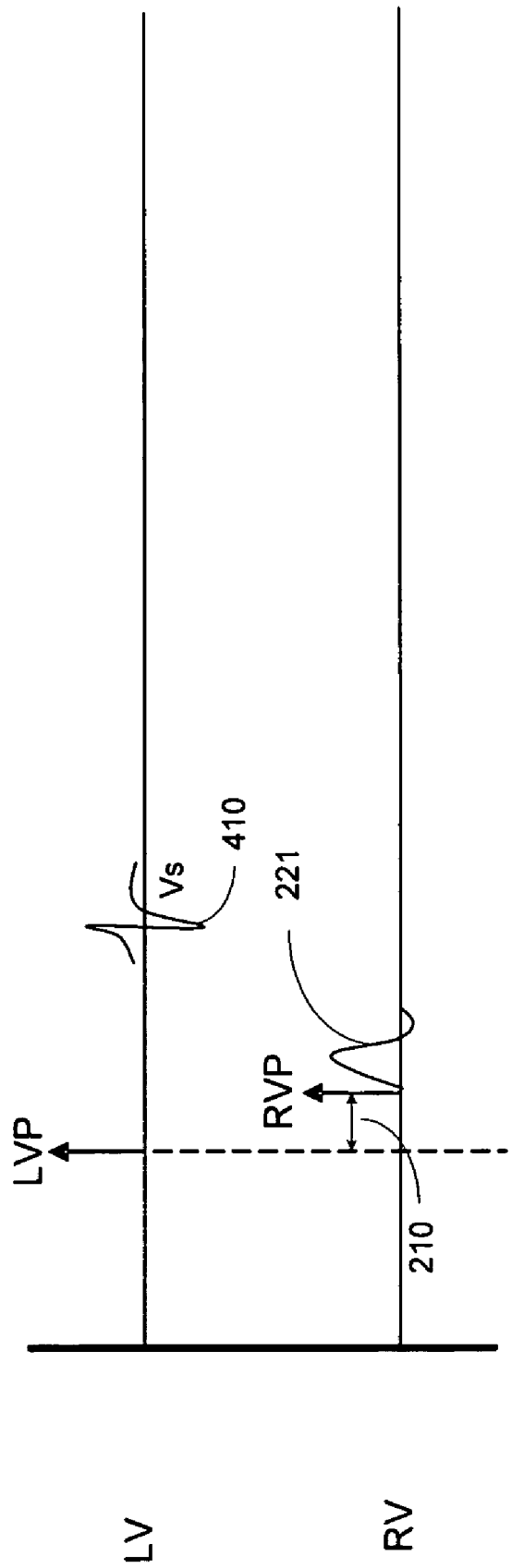
FIG. 4A is a timing diagram illustrating paced events and sensed signals for biventricular pacing resulting in right ventricular capture and left ventricular non-capture in accordance with embodiments of the invention.

The timing diagram of FIG. 4A illustrates paced events and sensed signals for biventricular pacing resulting from right ventricular capture and left ventricular non-capture. In this scenario, a left ventricular pacing pulse (LVP) is delivered to the left ventricle. A right ventricular pacing pulse (RVP) is delivered to the right ventricle slightly delayed from the time of delivery of the LVP. Delivery of the LVP and RVP may be separated in time by an interventricular delay 210, such as an interventricular delay 210 of about 40 ms or up to about 500 ms. In various embodiments, either the left ventricle or the right ventricle may be paced first.

In this example, the RVP captures the right ventricle producing a depolarization wavefront 221 initiated from the right ventricular site. The left ventricle is not captured by the LVP and initiation of a depolarization wavefront propagating from the left ventricle does not occur. Because the LVP did not produce capture, the left ventricular cardiac tissue does not become refractory. The non-refractoriness of the left ventricular cardiac tissue allows the right ventricular depolarization wavefront 221 to propagate to the left ventricle. A signal Vs 410 sensed at the left ventricular site indicates capture of the right ventricle and non-capture of the left ventricle.

The electrophysiological events described above may be used to determine capture of one or both chambers during biatrial, biventricular pacing and/or multisite pacing. Embodiments of the invention are directed to methods and systems for determining and using an intersite sensing interval in capture detection processes. Some embodiments involve biventricular pacing where the left and right ventricular paces are separated by an interventricular delay such that the left ventricle is paced prior to the right ventricle. This type of pacing is advantageous to facilitate synchrony between the left and right ventricular contractions where the contraction of the left ventricle is delayed with respect to the right ventricular contraction. An intersite sensing interval for sensing a depolarization propagated from the right ventricle to the left ventricle may be timed, for example, based on the timing of the delivery of the LVP or the timing of the delivery of the RVP. In one implementation, the pacemaker opens an intersite sensing interval following the first pacing pulse delivered to contralateral chambers. at the interchamber pacing delay plus the intersite conduction delay In some embodiments, the intersite sensing interval is based on measured conduction delays between the pacing sites. In these embodiments, prior to implementation of a capture detection process such as automatic capture detection or automatic capture threshold testing, an initialization procedure determines the measured conduction delay between pacing sites, e.g., right and left ventricles. The intersite sensing interval used for sensing depolarizations propagated to a pacing site from a remote pacing site may be determined based the measured conduction delay between the pacing site and the remote site. For example, in some embodiments, the timing of the intersite sensing interval is based on the pacing delay added to the measured intersite conduction delay.

The timing diagram of FIG. 4B illustrates, for two cardiac cycles 402, 402, the use of an intersite sensing interval 260 for capture and/or fusion detection in accordance with some embodiments. The first cardiac cycle 401 begins with a pace delivered to the right atrium (AP). A left ventricular pace (LVP) is delivered after an atrioventricular delay (AVD) 275 timed relative to the delivery of the atrial pace (AP). A right ventricular pace (RVP) is delivered offset in time from the LVP by an interventricular delay 210, such as an interventricular delay greater than about 40 ms. The RV-LV conduction delay 270 represents the time for a right ventricular depolarization to propagate to the left ventricle. In some implementations, the conduction delay 270 may be measured during an initialization process. The conduction delay 270 can be measured by delivering a pace to the right ventricle and determining the time for the depolarization wavefront initiated by the right ventricular pace to reach the left ventricle. A number of conduction measurements may be taken and the shortest conduction delay, the median conduction delay, the mean conduction delay measurement, or other value based on the measured conduction delays may be used for purposes of determining the intersite sensing interval.

The intersite sensing interval 260 is initiated based on the interventricular delay 210 and the intersite conduction delay 270. The intersite sensing interval 260 may begin anytime after the delivery of the RVP. In the example provided in FIG. 4B, the intersite sensing interval 260 begins slightly before the measured intersite conduction delay 270 ends which allows for beat-to-beat variations in the conduction delay. The next cardiac cycle 402 begins with the second atrial pulse (AP) which follows a ventriculoatrial (VA) delay 265.

The first cardiac cycle 401 illustrates LV non-capture. The propagated depolarization signal 290 sensed during the intersite sensing interval 260 indicates that the LV was not captured by the LVP. The second cardiac cycle 402 illustrates detection of a fusion beat. A depolarization signal 295 is sensed before the intersite sensing interval 260 begins indicates fusion. The sensed signal 295 cannot be a propagated depolarization from the RVP because the time of occurrence of the sensed signal 295 is insufficient to allow a depolarization wavefront initiated by the RVP to propagate to the LV. The sensed depolarization signal 295 must have some degree of intrinsic origin and thus is interpreted as fusion.

Figure 4C:
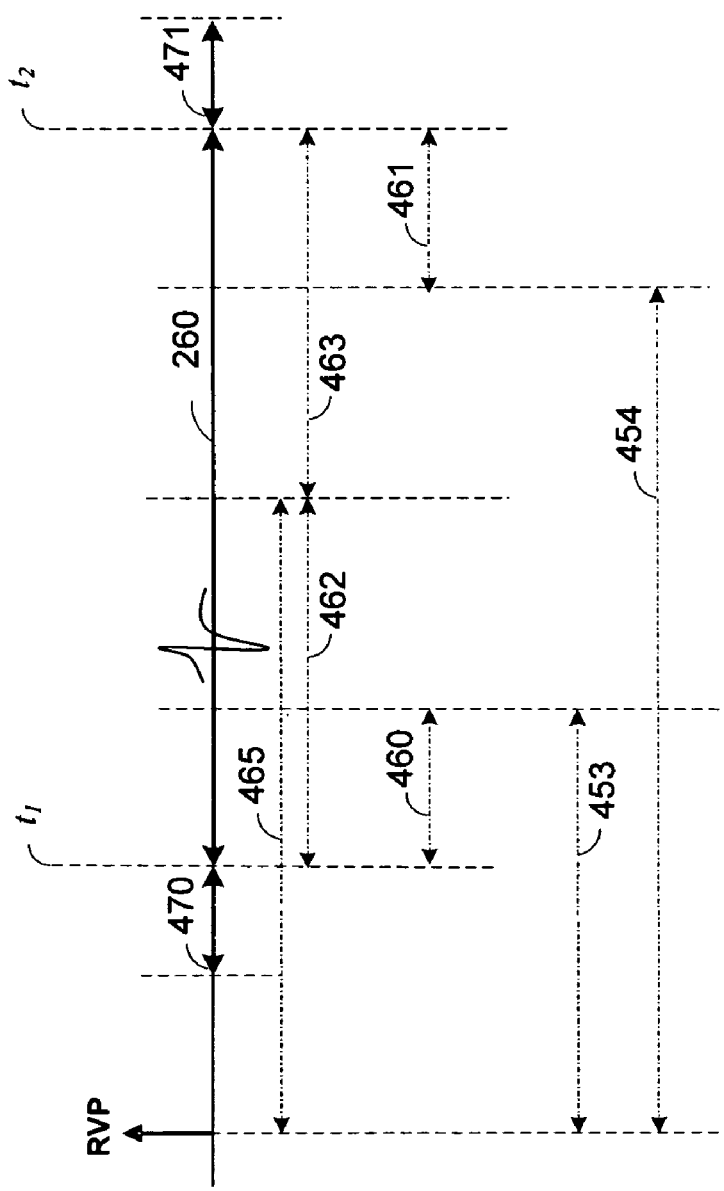
FIG. 4C illustrates selection of the start and end times of the intersite sensing interval and fusion detection intervals in accordance with embodiments of the invention.

FIG. 4C illustrates selection of the timing for the intersite sensing interval 260 in more detail. The intersite sensing interval starts at time $t_1$ and extends to time $t_2$. Start time $t_1$ and end time $t_2$ may be selected based on intersite conduction delay and the measured values of the intersite conduction delay. For example, in one implementation, the average conduction delay 465 is determined from multiple measurements of the conduction delay. The intersite sensing interval 260 may be selected based on the average conduction delay 465. For example, the start time $t_1$ and may be selected as a predetermined time 462 prior to the average conduction delay 465 and the end time $t_2$ of the intersite sensing interval may be selected to be a predetermined time 463 after the average conduction delay 465.

In situations where the sample of measured conduction delays is not a normal distribution, conduction delay measurements other than the average value may be used. For example, in one implementation, the shortest conduction delay 453 and the longest conduction delay 454 are determined from the multiple conduction delay measurements. The start time $t_1$ of the intersite sensing interval is selected as a predetermined time 460 prior to the shortest measured conduction delay 453. The end time $t_2$ of the intersite sensing interval is selected as a predetermined time 461 after the longest measured conduction delay 454.

Alternatively, other values derived from the measured conduction delays, e.g., mean and standard deviation, may be used to determine the start and end times $t_1$, $t_2$ of the intersite sensing interval 260.

FIG. 4C also illustrates fusion detection intervals 470, 471 before and after the intersite sensing interval 260. If a depolarization is detected within one of the fusion detection intervals 470, 471, fusion is detected.

Figure 5A:
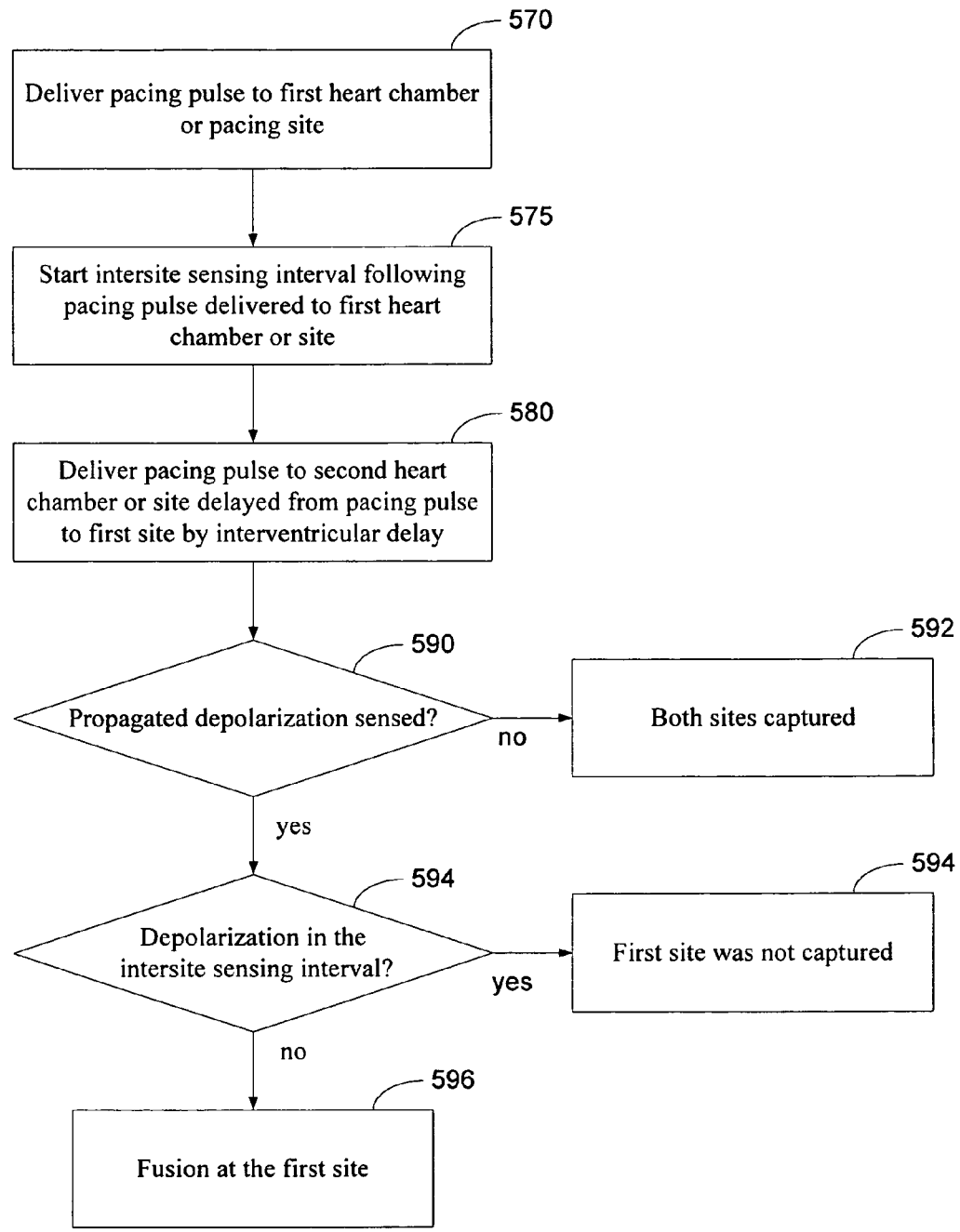
FIG. 5A is a flowchart illustrating a capture detection method in accordance with embodiments of the invention.

The flowchart of FIG. 5A illustrates a method for detecting capture in accordance with embodiments of the invention. A pacing pulse is delivered 570 to a first heart chamber or first pacing site. An intersite sensing interval begins 575 following the delivery of the pacing pulse to the first site. The timing of the intersite sensing interval is based on an intersite pacing delay and the intersite conduction delay.

A pacing pulse is delivered 580 to the second site. The pacing pulse delivered to the second site is delayed from the pacing pulse delivered to the first site by the intersite pacing delay. If a depolarization propagated from the second site to the first site is not sensed 590 during the intersite sensing interval, then both sites were captured 592. If a depolarization propagated from the second site to the first site is sensed 590 during the intersite sensing interval, then the pacing pulse delivered to the first site did not produce 594 capture at the first site.

A fusion beat may occur when an intrinsic cardiac depolarization of a particular chamber or site merges with a depolarization from a pacing pulse. If the propagated depolarization is sensed, but it is not sensed within the intersite sensing interval, then fusion is detected 596. Fusion beats are detected outside the intersite sensing interval because there is a finite or defined time required for the wavefront to propagate between pacing sites. Regardless of where the fusion of the intrinsic and paced activations occurred, if the sensed event at the first paced site occurs before the earliest possible propagation time between the sites, then the activation must have some degree of intrinsic origin and thus be fusion.

Figure 5B:
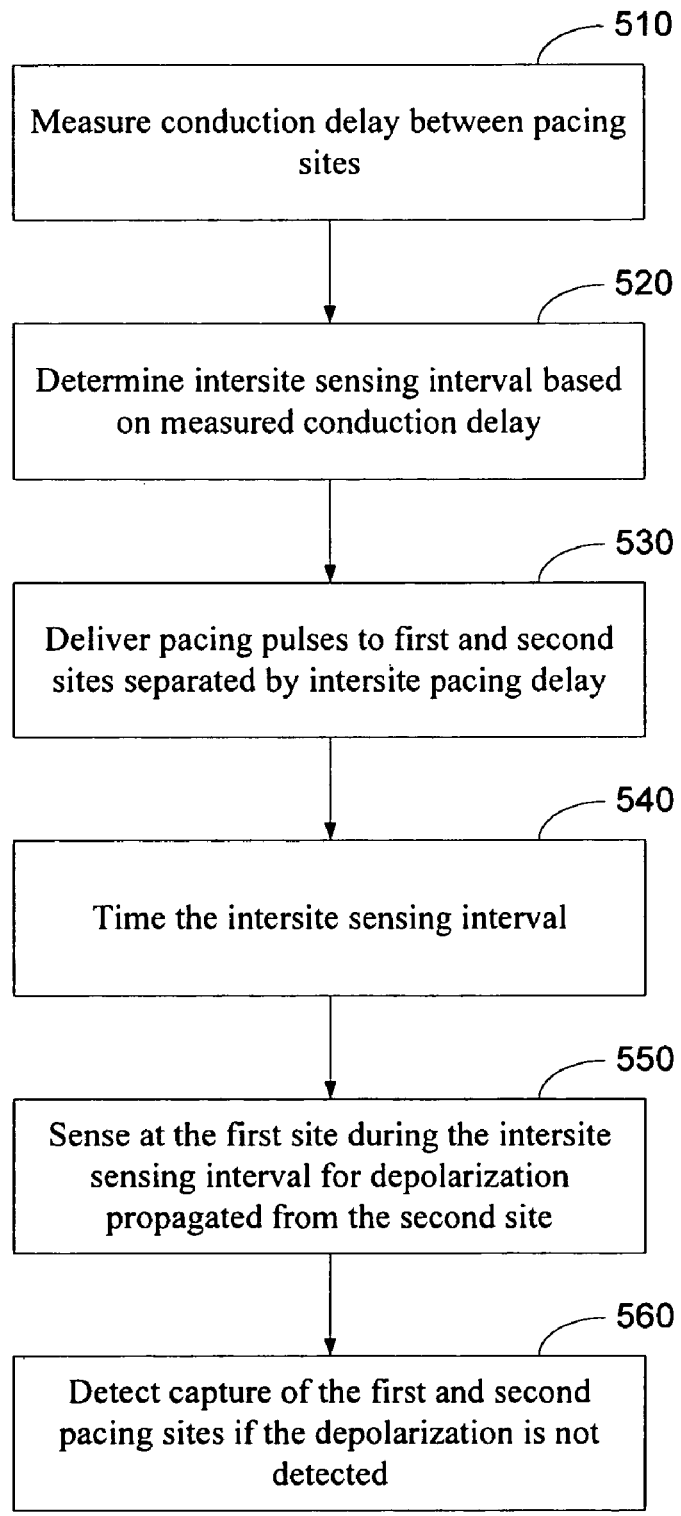
FIG. 5B is a flowchart illustrating a method for detecting capture using an intersite sensing interval based on the measured intersite conduction delay between two pacing sites.

The flowchart of FIG. 5B illustrates a method for detecting capture using an intersite sensing interval based on the measured intersite conduction delay between the second site and the first site. During an initialization phase, the conduction delay between second site and the first site is measured 510. The intersite sensing interval used for capture detection is determined 520 from the measured conduction delay. Pacing pulses are delivered 530 to first and second pacing sites using an intersite pacing delay between the pacing pulses. The use of an intersite pacing delay shifts the interaction point of the depolarization wavefronts closer to the second site, thus exaggerating the intersite conduction delay and facilitating detection of a propagated depolarization wave. Adjusting the intersite pacing delay is important to avoid fusion and depends on the relative location of the electrodes. Given a fusion outcome from FIG. 5A, modifications to the intersite pacing delay may enhance the capture detection performance. For example, the intersite pacing delay may be adjusted to ensure the intersite pacing delay is large enough so that propagated activation will not be lost during the blanking period. Also by prolonging the intersite pacing delay, the likelihood that the sensed event is a true depolarization and not noise or pacing artifact is increased.

The intersite sensing interval may be timed 540 following delivery of the pacing pulse to the first site. For example, the timing of the intersite sensing interval may be based on the intersite pacing delay and the measured intersite conduction delay. During the intersite sensing interval, the system senses 550 at the first pacing site for a depolarization propagated from the second pacing site. If the propagated depolarization from the second site is not detected 560, both pacing sites were captured. If the propagated depolarization is detected, then the pacing pulse delivered to the first pacing site did not produce capture at the first pacing site.

The propagated depolarization may be detected by evaluating characteristics of the cardiac signal sensed at the first site. For example, the capture detection circuitry may evaluate the peak value, rise time, peak width, slope, timing, and/or other morphological characteristics of the sensed signal to determine if the sensed signal represents a propagated depolarization.

Those skilled in the art will appreciate that reference to a capture threshold testing procedure indicates a method of determining the capture threshold at a pacing site in the left atrium, the right atrium, the left ventricle or the right ventricle. In such a procedure, a pacemaker, automatically or upon command, initiates a search for the capture threshold of the selected site. The capture threshold may be defined as the lowest pacing energy that consistently produces a contraction at the pacing site. Programmable pacemakers enable the amplitude and pulse width of pacing pulses to be adjusted to a value that exceeds the measured capture threshold.

In one example of an automatic capture threshold procedure, the pacemaker delivers a sequence of pacing pulses to the heart and detects the cardiac responses to the pacing pulses as described herein. The energy of the pacing pulses delivered to one site may be decreased in discrete steps until a predetermined number of loss-of-capture events occur. After the predetermined number of loss-of-capture events occur, the pacemaker may increase the stimulation energy in discrete steps until a predetermined number of capture events occur to confirm the capture threshold. A capture threshold test may be performed using the methods of the present invention.

Other procedures for implementing capture threshold testing may be utilized. In one example, the pacing energy may be increased in discrete steps until capture is detected. In another example, the pacing energy may be adjusted according to a binomial search pattern, a binary search pattern, a random search pattern, or other search patterns for example.

Automatic capture threshold testing is distinguishable from automatic capture detection which is a procedure that may occur on a beat-by-beat basis during pacing. Automatic capture detection verifies that a delivered pacing pulse results in a captured response. When a captured response is not detected following a pace pulse, the pacemaker may deliver a back up pace to ensure consistent pacing. The back up pace may be delivered, for example, about 90-110 ms after the initial pacing pulse. If a predetermined number of pacing pulses delivered during normal pacing do not produce a captured response, the pacemaker may initiate a capture threshold test to reevaluate the capture threshold. Automatic capture detection and back up pacing may be implemented using the capture detection processes of the present invention.

The embodiments of the present system illustrated herein are generally described as being implemented in a cardiac rhythm management (CRM) system incorporating the functions of a cardiac pacemaker that may operate in numerous pacing modes known in the art. The CRM system may optionally include circuitry for delivering cardiac defibrillation. Various types of multisite implantable pacemakers are known in the art and may be used in connection with the capture detection methods of the present invention.

Although the present system is described in conjunction with an implantable CRM system having a microprocessor-based architecture, it will be understood that the implantable CRM system (or other device) may be implemented in any logic-based integrated circuit architecture, if desired.

Figure 6:
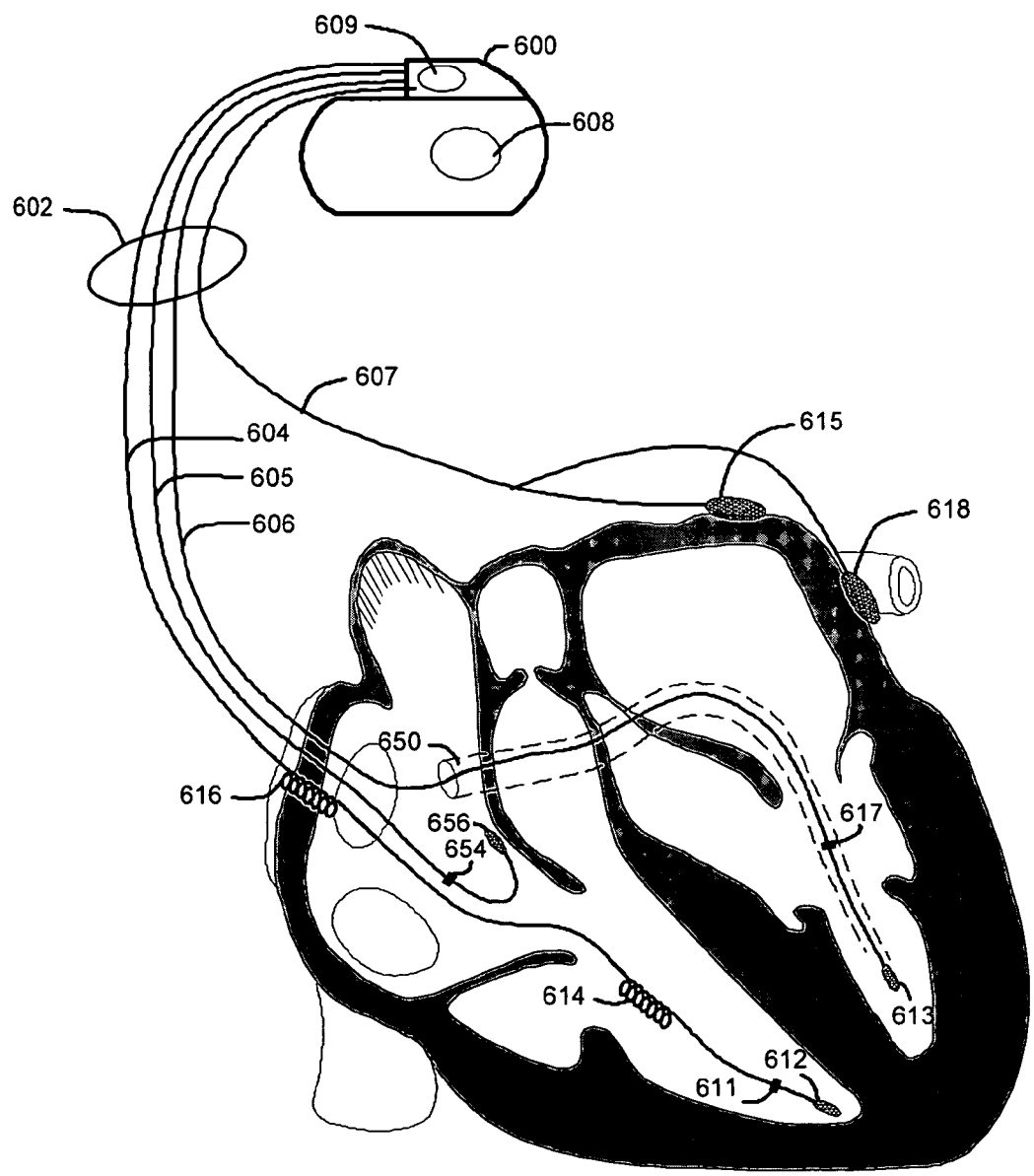
FIG. 6 illustrates a partial view of a cardiac rhythm management system that may be used to implement capture detection methods of in accordance with embodiments of the invention.

Referring now to FIG. 6 of the drawings, there is shown a CRM system that may be used to implement capture detection approaches of the present invention. The CRM system in FIG. 6 includes a pacemaker 600 (or optionally a pacemaker/defibrillator) enclosed within a housing and coupled to a lead system 602. The housing and/or header of the pacemaker 600 may incorporate one or more can or indifferent electrodes 608, 609 used to provide electrical stimulation energy to the heart and/or to sense cardiac electrical activity. The pacemaker 600 may utilize all or a portion of the pacemaker housing as a can electrode 608. The pacemaker 600 may include an indifferent electrode 609 positioned, for example, on the header or the housing of the pacemaker 600. If the pacemaker 600 includes both a can electrode 608 and an indifferent electrode 609, the electrodes 608, 609 typically are electrically isolated from each other.

The lead system 602 is used to detect cardiac electrical signals produced by the heart and to provide electrical energy to the heart under certain predetermined conditions to treat cardiac arrhythmias. The lead system 602 may include one or more electrodes used for pacing, sensing, and/or defibrillation. In the embodiment shown in FIG. 6, the lead system 602 includes an intracardiac right ventricular (RV) lead system 604, an intracardiac right atrial (RA) lead system 605, and an intracardiac left ventricular (LV) lead system 606. An extracardiac left atrial (LA) lead system 607 is employed.

The CRM system illustrated in FIG. 6 is configured for biventricular or biatrial pacing. The lead system 602 of FIG. 6 illustrates one embodiment that may be used in connection with the capture detection processes described herein. Other leads and/or electrodes may additionally or alternatively be used. For example, a CRM system may be configured for intrachamber pacing. In this configuration, the CRM system may pace multiple sites in one cardiac chamber via multiple electrodes within the chamber. This type of multisite pacing may be employed in one or more of the right atrium, left atrium, right ventricle or left ventricle. Multisite pacing in a chamber may be used for example, to increase the power and or synchrony of cardiac contractions of the paced chamber.

The lead system 602 may include intracardiac leads 604, 605, 606 implanted in a human body with portions of the intracardiac leads 604, 605, 606 inserted into a heart. The intracardiac leads 604, 605, 606 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 6, the lead system 602 may include one or more extracardiac leads 607 having electrodes 615, 618, e.g., epicardial electrodes, positioned at locations outside the heart for sensing and pacing one or more heart chambers. In some configurations, the epicardial electrodes may be placed on or about the outside of the heart and/or embedded in the myocardium from the locations outside the heart.

The right ventricular lead system 604 illustrated in FIG. 6 includes an SVC-coil 616, an RV-coil 614, an RV-ring electrode 611, and an RV-tip electrode 612. The right ventricular lead system 604 extends through the right atrium and into the right ventricle. In particular, the RV-tip electrode 612, RV-ring electrode 611, and RV-coil electrode 614 are positioned at appropriate locations within the right ventricle for sensing and delivering electrical stimulation pulses to the heart. The SVC-coil 616 is positioned at an appropriate location within the right atrium chamber of the heart or a major vein leading to the right atrial chamber.

In one configuration, the RV-tip electrode 612 referenced to the can electrode 608 may be used to implement unipolar pacing and/or sensing in the right ventricle. Bipolar pacing and/or sensing in the right ventricle may be implemented using the RV-tip 612 and RV-ring 611 electrodes. In yet another configuration, the RV-ring 611 electrode may optionally be omitted, and bipolar pacing and/or sensing may be accomplished using the RV-tip electrode 612 and the RV-coil 614, for example. The right ventricular lead system 604 may be configured as an integrated bipolar pace/shock lead. The RV-coil 614 and the SVC-coil 616 are defibrillation electrodes.

The left ventricular lead 606 includes an LV distal electrode 613 and an LV proximal electrode 617 located at appropriate locations in or about the left ventricle for pacing and/or sensing the left ventricle. The left ventricular lead 606 may be guided into the right atrium of the heart via the superior vena cava. From the right atrium, the left ventricular lead 606 may be deployed into the coronary sinus ostium, the opening of the coronary sinus 650. The lead 606 may be guided through the coronary sinus 650 to a coronary vein of the left ventricle. This vein is used as an access pathway for leads to reach the surfaces of the left ventricle which are not directly accessible from the right side of the heart. Lead placement for the left ventricular lead 606 may be achieved via subclavian vein access and a preformed guiding catheter for insertion of the LV electrodes 613, 617 adjacent to the left ventricle.

Unipolar pacing and/or sensing in the left ventricle may be implemented, for example, using the LV distal electrode referenced to the can electrode 608. The LV distal electrode 613 and the LV proximal electrode 617 may be used together as bipolar sense and/or pace electrodes for the left ventricle. The lead system 602 in conjunction with the pacemaker 600 may provide bradycardia pacing therapy to maintain a hemodynamically sufficient heart rate. The left ventricular lead 606 and the right ventricular lead 604 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from congestive heart failure.

The right atrial lead 605 includes a RA-tip electrode 656 and an RA-ring electrode 654 positioned at appropriate locations in the right atrium for sensing and pacing the right atrium. In one configuration, the RA-tip 656 referenced to the can electrode 608, for example, may be used to provide unipolar pacing and/or sensing in the right atrium. In another configuration, the RA-tip electrode 656 and the RA-ring electrode 654 may be used to effect bipolar pacing and/or sensing.

Figure 7:
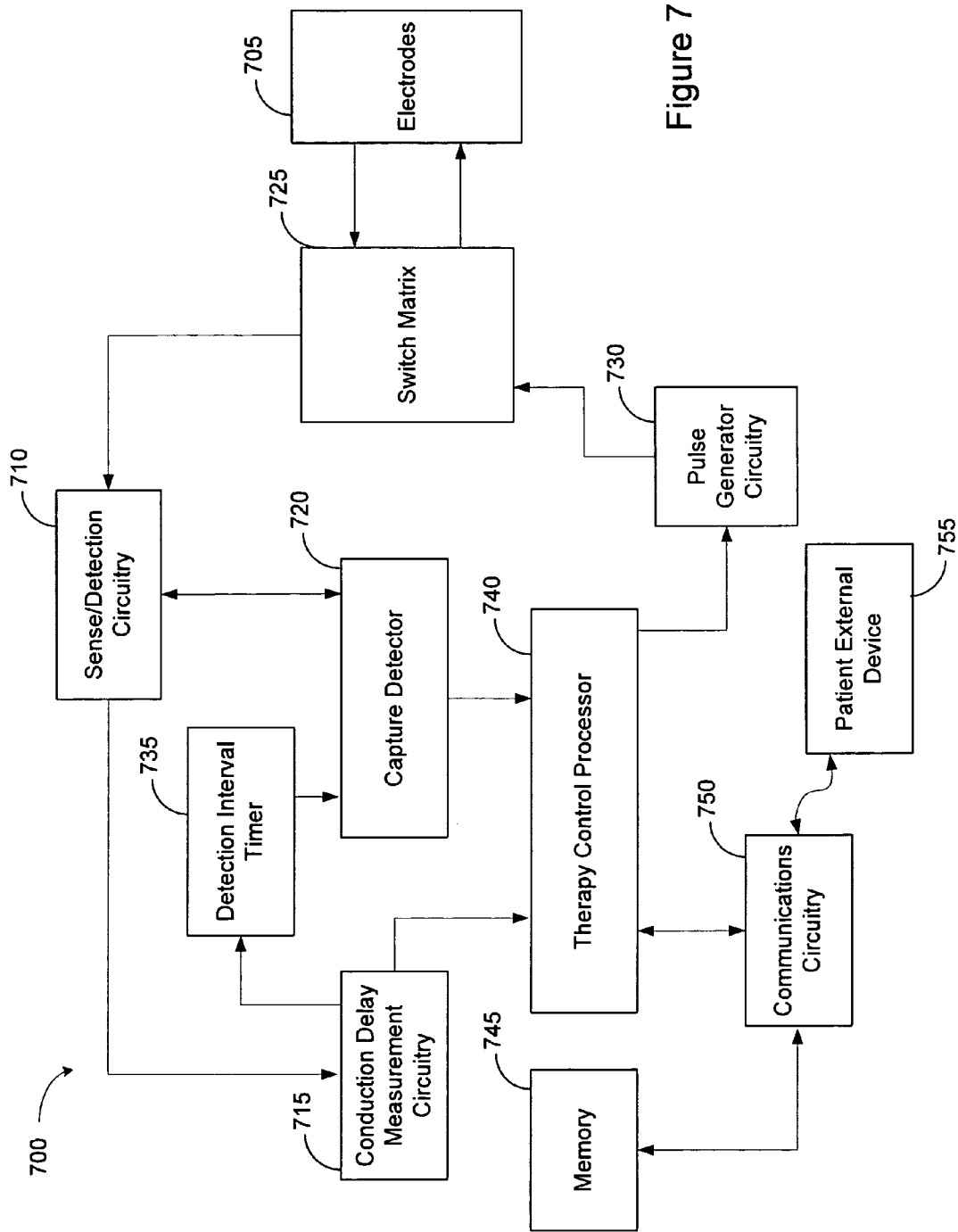
FIG. 7 shows a block diagram of an embodiment of a cardiac rhythm management system suitable for implementing a capture detection methodology of the present invention.

Referring now to FIG. 7, there is shown a block diagram of an embodiment of an implantable CRM system 700 suitable for implementing capture detection approaches of the present invention. FIG. 7 shows a CRM system 700 divided into functional blocks. It is understood by those skilled in the art that there exist many possible configurations in which these functional blocks can be arranged. The example depicted in FIG. 7 is one possible functional arrangement. Other arrangements are also possible. For example, more, fewer or different functional blocks may be used to describe a cardiac system suitable for implementing the capture detection processes of the present invention. In addition, although the CRM system 700 depicted in FIG. 7 contemplates the use of a programmable microprocessor-based logic circuit, other circuit implementations may be utilized.

The CRM system 700 includes a therapy control processor 740 capable of detecting arrhythmias and controlling the delivery of pacing pulses and/or other forms of electrical stimulation to treat the arrhythmias. The CRM system 700 includes pulse generator circuitry 730 configured to generate pulses for treating bradyarrhythmia and, optionally, for generating high energy defibrillation or cardioversion stimulation to the heart for terminating dangerous tachyarrhythmias.

The pacing and/or defibrillation pulses are delivered via multiple cardiac electrodes 705 electrically coupled to a heart and disposed at multiple locations within, on, or about the heart. One or more electrodes 705 may be disposed in, on, or about each heart chamber or at multiple sites of one heart chamber. The electrodes 705 are coupled to switch matrix 725 circuitry used to selectively couple electrodes 405 to sense circuitry 710 and/or the pulse generator circuitry 730. Sensed signals may be used by the conduction delay measurement circuitry 715 to measure the conduction delay between cardiac pacing sites.

Measurement of the conduction delay may be implemented as follows: The pulse generator circuitry 730, under control of the control processor 740 delivers a pacing pulse to a pacing site (designated the second pacing site) via the switch matrix 725 and selected electrode(s) at the pacing site. The sense circuitry 710 senses electrical signals at another pacing site (designated the first pacing site) via the switch matrix 725 and selected electrode(s) at the first pacing site.

The conduction delay measurement circuitry 715 measures the interval of time between the pacing pulse delivered to the second site and the depolarization signal propagated from the second site to the first site where the propagated depolarization is sensed. The measured conduction delay may be used to determine an intersite sensing interval for capture detection in accordance with embodiments of the invention. The intersite sensing interval is timed for the capture detection by the intersite interval timer 735.

Various embodiments of the invention involve an intersite sensing interval for capture detection that is based on the intersite pacing delay and/or the intersite conduction delay. In certain embodiments, for example, the intersite sensing interval comprises an interval that is initiated based on the intersite pacing delay and the conduction time between the first pacing site and the second pacing site. In some embodiments, the conduction time used to develop the intersite sensing interval is the conduction time measured by the conduction delay measurement circuitry 715.

In other embodiments, the conduction time used to develop the intersite sensing interval is a conduction time programmed into the CRM system 700 based on electrophysiological studies or other methods for measuring or estimating the conduction time between pacing sites. In these embodiments, the measured or estimated conduction time may be input to the CRM system 700, along with other data, through a patient-external device 755 via telemetry-based communications circuitry 750. Data and/or program commands useful for controlling the operation of the CRM device 700 may be transmitted via the patient external device 755 and communications circuitry 750 and stored in the memory 745 of the CRM system 700.

The conduction delay measurement circuitry 715 of the CRM system 700 advantageously supplies a recent measurement of the conduction delay and may also have the ability to perform a conduction delay measurement, for example, in conjunction with an initialization process of an automatic capture threshold test.

The capture detector 720 uses the intersite sensing interval to determine capture of a first pacing site based on propagated depolarization from a second site remote from the first site. As previously described, pacing pulses are delivered to the first and second pacing sites separated in time by an intersite pacing delay. The intersite pacing delay may be selected, for example, to promote synchronous contraction of two chambers when pacing sites are located in two contralateral chambers. The intersite pacing delay may also be used to increase the power of a contraction of a single chamber when multiple intrachamber sites are used, or to achieve other beneficial hemodynamic effects. The capture detector 720 senses for the propagated depolarization. Capture, noncapture or fusion may be detected based on if and when the propagated depolarization is sensed relative to the intersite sensing interval.

Figure 8A:
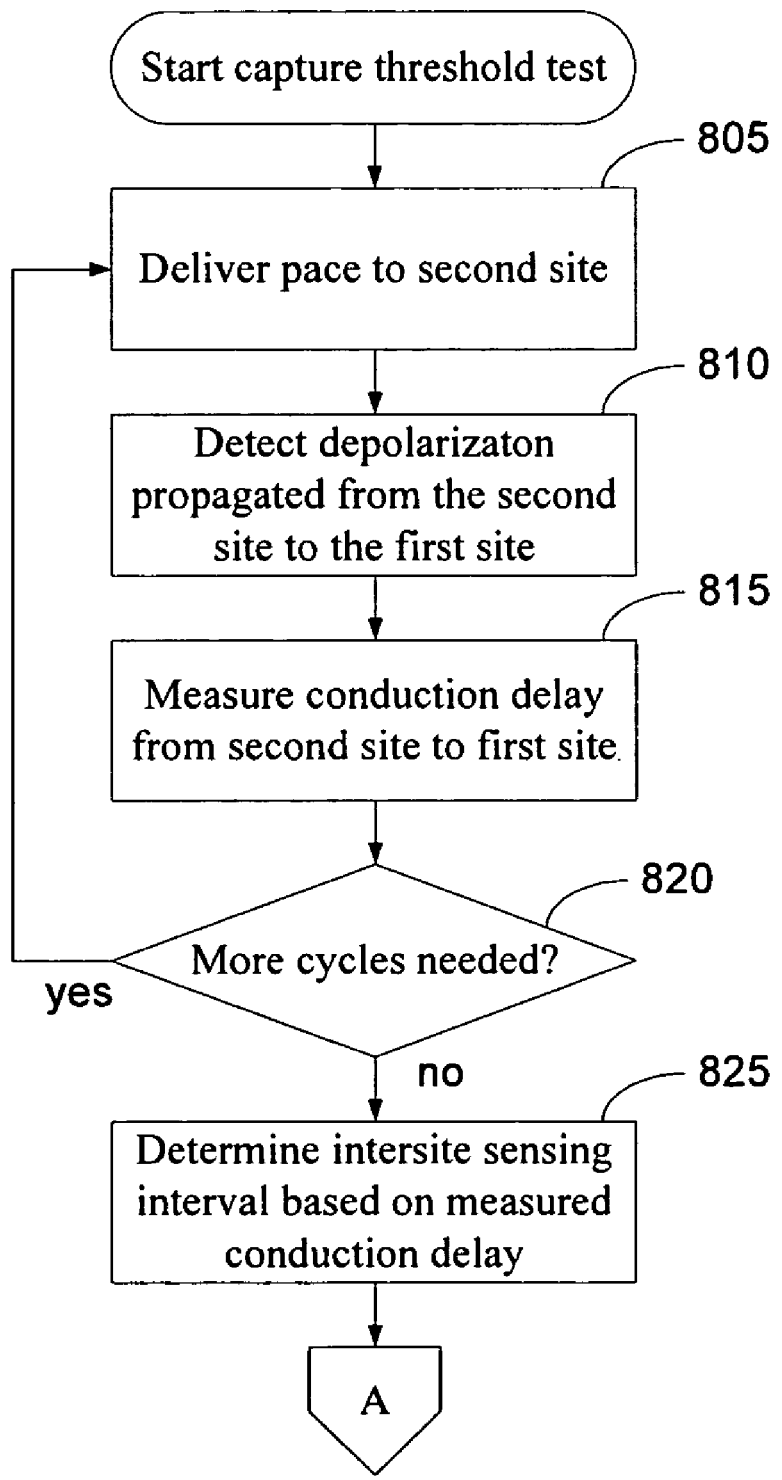
FIGS. 8A and 8B illustrate a flowchart of a capture threshold testing method in accordance with embodiments of the invention.
Figure 8B:
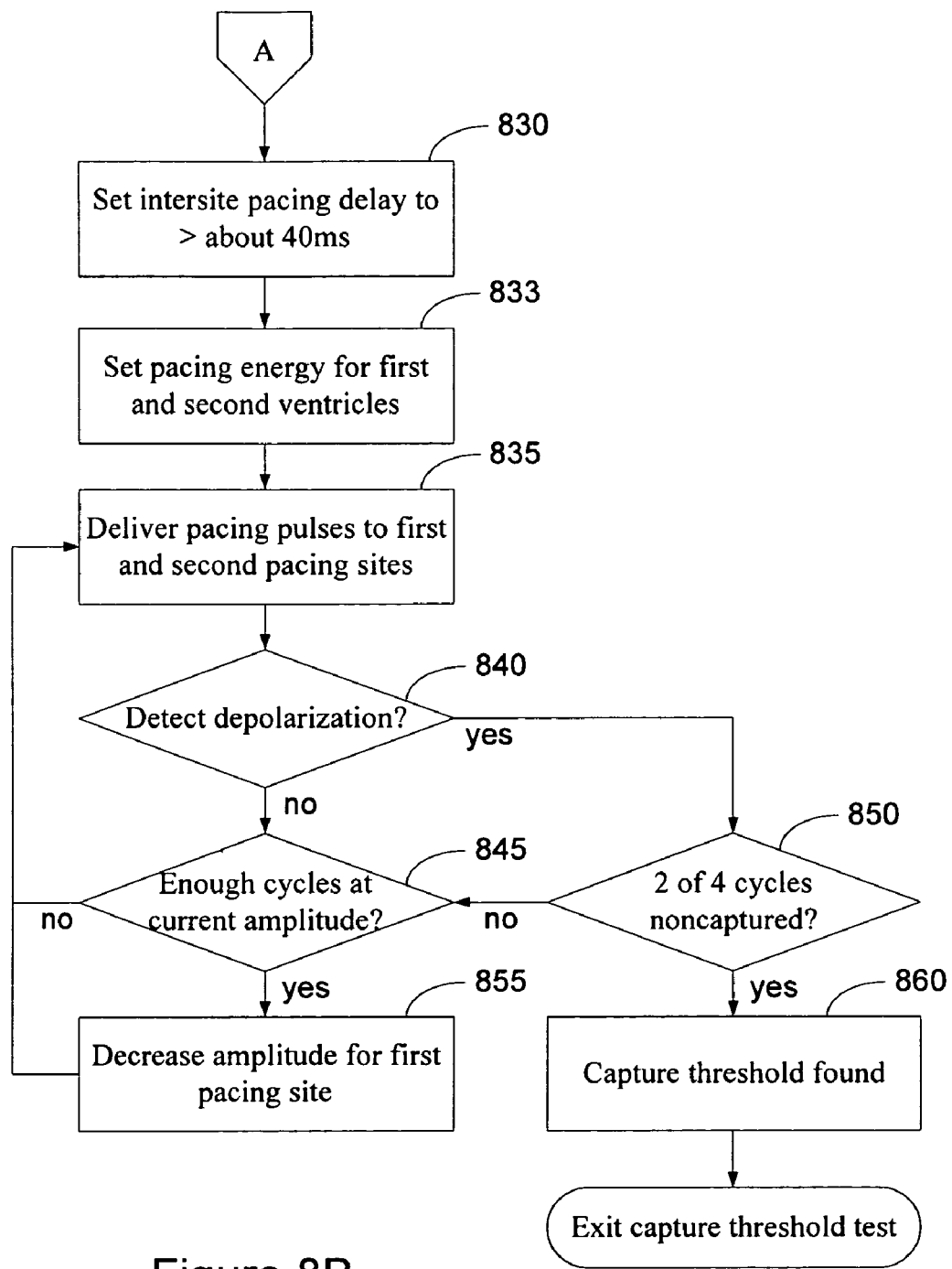

The flowchart of FIGS. 8A and 8B illustrate a method of performing a capture threshold test using the capture detection approaches of the present invention. The capture threshold test described in this example uses biventricular pacing in a step down threshold test procedure, although other procedures for capture threshold determination, such as step up, binary search, or other search patterns are also possible. In the test illustrated by FIGS. 8A and 8B, the energy of pacing pulses delivered to a first ventricle are stepped down, while the energy of pacing pulses delivered to a second contralateral ventricle are maintained at a level that ensures capture of the second ventricle.

During an initialization portion of the test, an intersite sensing interval is determined. During a step down portion of the test, the pacing energy delivered to the first ventricle is decreased until loss of capture is detected and the capture threshold of the first ventricle is determined.

The capture threshold test illustrated in FIGS. 8A and 8B includes an initialization process 805-825 that measures the conduction delay between pacing sites in the first and second ventricles prior to performing the step down portion of the test. During each initialization cycle, a biventricular pacing pulses are delivered 805 to the ventricles following an atrio-ventricular (AV) delay initiated by an atrial pace or intrinsic atrial depolarization. The biventricular pacing pulses are delivered using an interventricular pacing delay, where the interventricular pacing delay may be greater than about 40 ms, which is a good estimate of blanking time following the pace, for example.

The system senses in a first ventricle for a depolarization propagated 810 from the second ventricle to the first ventricle. The interventricular conduction delay is measured 815 as the interval of time between pacing pulse delivered to the second ventricle and the detection of the propagated depolarization at the first ventricle. The process continues until conduction delays have been measured 820 for a predetermined number of cycles.

An intersite sensing interval is determined 825 based on the measured conduction delays. For example, the intersite sensing interval may include the interventricular pacing delay added to the interventricular conduction delay. The interventricular conduction delay is determined from the multiple conduction measurements acquired during the initialization portion 805-825 of the capture threshold test. According to various approaches, the intersite sensing interval may be determined based on a shortest conduction delay of the multiple conduction delays, longest conduction delay of the multiple measured conduction delays, a most recent conduction delay, a median measured conduction delay, mean measured conduction delay, or may be based on a combination of the multiple measured conduction delays. For example, the intersite sensing interval may be determined based on an average, weighted average, or other linear combination of the conduction delays measured for the multiple cycles.

After the initialization portion 805-825 of the capture threshold test is complete, the step down portion 830-860 begins. The AV delay and the interventricular pacing delay are set 830 to the values used during the initialization portion 805-825 of the test. Pacing energies for the left and right ventricles are set 833 to initially high values to ensure capture of both chambers. Biventricular pacing pulses are delivered 835 to the first and second ventricles in accordance with the AV and interventricular pacing delays used in the initialization process.

During the intersite sensing interval, the system senses in the first ventricle for the depolarization propagated from the second ventricle to the first ventricle. In this and the interventricular conduction delay determined during the initialization portion. If a propagated depolarization is sensed 840 in the first ventricle, the system checks 845 whether enough cycles (e.g., about three cycles) have been delivered at the current pacing energy. If not, another cycle is performed at the current pacing energy. If so, the system decreases 855 the pacing energy of the first chamber and the test continues at the stepped down energy.

A propagated depolarization sensed 840 at the first chamber indicates noncapture. If 2 of 4 cycles, or other appropriate percentage, are not captured 850, the system recognizes loss of capture and determines 860 the capture threshold.

A capture detection approach according to the present invention may include one or more of the features, structures, methods, or combinations thereof described herein. For example, a cardiac device may be implemented to include one or more of the advantageous features and/or processes described. It is intended that such a device need not include all of the features described herein, but may be implemented to include selected features that provide for useful structures and/or functionality.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method, implementable in a pacemaker, for detecting capture, comprising:
   determining an intersite sensing interval based on an intersite pacing delay and an intersite conduction delay associated with first and second pacing sites;
   delivering pacing pulses to the first pacing site and the second pacing site, the pacing pulses separated in time by the intersite pacing delay;
   timing the intersite sensing interval;
   during the intersite sensing interval, sensing at the first pacing site for a depolarization propagated to the first pacing site from the second pacing site; and
   detecting capture of the first pacing site and the second pacing site if the depolarization propagated from the second pacing site is not sensed, wherein determining the intersite sensing interval, delivering the pacing pulses, timing the intersite sensing interval, and detecting capture are performed by the pacemaker.

2. The method of claim 1, wherein the intersite pacing delay is selected to shift the interaction point of the depolarization propagated from the second pacing site and a depolarization propagated from the first pacing site.

3. The method of claim 1, further comprising detecting non-capture of the first pacing site if the depolarization propagated from the second pacing site is sensed within the intersite sensing interval.

4. The method of claim 1, further comprising detecting fusion if a depolarization signal is sensed before or after the intersite sensing interval.

5. The method of claim 1, wherein the intersite pacing delay is greater than about 40 ms.

6. The method of claim 1, further comprising modifying an amplitude of pacing pulses delivered to the first pacing site during successive cardiac cycles until loss of capture of the first pacing site is detected.

7. The method of claim 6, further comprising determining a capture threshold of the first pacing site after loss of capture at the first pacing site is detected.

8. The method of claim 1, further comprising measuring the conduction delay.

9. The method of claim 8, wherein measuring the conduction delay comprises measuring the conduction delay during an initialization process of a capture threshold test.

10. A pacemaker, comprising:
- electrodes configured to be electrically coupled to a heart at a first pacing site and a second pacing site;
- pacing circuitry configured to deliver pacing pulses to the first pacing site and the second pacing site via the electrodes, the pacing pulses separated in time by an intersite pacing delay;
- timer circuitry configured to time an intersite sensing interval, the intersite sensing interval determined based on the intersite pacing delay and a conduction delay associated with the first and second pacing sites;
- sense circuitry configured to sense at the first pacing site during the intersite sensing interval for a depolarization propagated from the second pacing site responsive to the pacing pulse delivered to the second pacing site;
- capture detection circuitry configured to detect capture of the first and second pacing sites if the depolarization propagated from the second pacing site is not sensed.

11. The pacemaker of claim 10, further comprising measurement circuitry configured to measure the conduction delay associated with the first and second pacing sites.

12. The pacemaker of claim 10 wherein:
the first pacing site comprises a ventricle; and
the second pacing site comprises a contralateral ventricle.

13. The pacemaker of claim 10, wherein:
the first pacing site comprises an atrium; and
the second pacing site comprises a contralateral atrium.

14. The pacemaker of claim 10, wherein the first and second pacing sites comprise intrachamber pacing sites.

15. The pacemaker of claim 10, wherein the capture detection circuitry is configured to detect non-capture of the first pacing site if the depolarization propagated from the second pacing site is detected during the intersite sensing interval.

16. The pacemaker of claim 10, wherein the capture detection circuitry is configured to detect fusion if a depolarization signal is detected before or after the intersite sensing interval.

17. The pacemaker of claim 10, further comprising circuitry configured to control a capture threshold test, the control circuitry configured to modify an energy of the pacing pulse delivered to the first pacing site until loss of capture is detected.

18. The pacemaker of claim 10, wherein the intersite pacing delay is greater than about 40 ms.

19. The pacemaker of claim 10, wherein the intersite pacing delay is selected to shift the interaction point of the depolarization propagated from the second pacing site and a depolarization propagated from the first pacing site.

20. A pacemaker system, comprising:
- means for determining an intersite sensing interval based on an intersite pacing delay and an intersite conduction delay associated with first and second pacing sites;
- pacing circuitry configured to deliver pacing pulses to the first pacing site and the second pacing site, the pacing pulses separated in time by the intersite pacing delay;
- means for timing the intersite sensing interval;
- means for sensing, during the intersite sensing interval, at the first pacing site for a depolarization propagated to the first pacing site from the second pacing site; and
- means for detecting capture of the first pacing site and the second pacing site if the depolarization propagated from the second pacing site is not sensed.

21. The system of claim 20, further comprising means for detecting non-capture of the first pacing site if the depolarization propagated from the second pacing site is sensed within the intersite sensing interval.

22. The system of claim 20, further comprising means for detecting fusion if the depolarization propagated from the second pacing site is sensed outside the intersite sensing interval.

* * * * *